United States Patent
Woerlee et al.

(10) Patent No.: US 11,000,197 B2
(45) Date of Patent: May 11, 2021

(54) BLOOD PRESSURE MONITOR

(71) Applicant: KONINKLIJKE PHILIPS N.V., Eindhoven (NL)

(72) Inventors: Pierre Hermanus Woerlee, Valkenswaard (NL); Paul Aelen, Eindhoven (NL); Maarten Petrus Joseph Kuenen, Veldhoven (NL); Nicolaas Lambert, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 351 days.

(21) Appl. No.: 16/083,574

(22) PCT Filed: Mar. 21, 2017

(86) PCT No.: PCT/EP2017/056607
§ 371 (c)(1),
(2) Date: Sep. 10, 2018

(87) PCT Pub. No.: WO2017/162616
PCT Pub. Date: Sep. 28, 2017

(65) Prior Publication Data
US 2019/0090763 A1    Mar. 28, 2019

(30) Foreign Application Priority Data

Mar. 23, 2016 (EP) .................................. 16161953

(51) Int. Cl.
*A61B 5/0225* (2006.01)
*A61B 5/022* (2006.01)
(Continued)

(52) U.S. Cl.
CPC ........ *A61B 5/02255* (2013.01); *A61B 5/0295* (2013.01); *A61B 5/02225* (2013.01);
(Continued)

(58) Field of Classification Search
CPC ........ A61B 2562/0247; A61B 5/02255; A61B 5/0295; A61B 5/1073; A61B 5/6831
See application file for complete search history.

(56) References Cited

U.S. PATENT DOCUMENTS

| 2,667,159 A | 1/1954 | Goldberg |
| 4,494,553 A | 1/1985 | Sciarra |

(Continued)

OTHER PUBLICATIONS

Wax, et al., "Invasive and Concomitant Noninvasive Intraoperative Blood Pressure Monitoring"; Anesthesiology, V 115 • No. 5, Nov. 2011.
(Continued)

*Primary Examiner* — Christine H Matthews (57) ABSTRACT

There is provided a blood pressure monitor for use in measuring the blood pressure of a subject, the blood pressure monitor comprising a cuff that is configured to be placed around a body part of the subject and inflated to apply pressure to the body part; a pressure sensor that is configured to provide measurements of the pressure in the cuff; a plethysmography sensor comprising a coil having one or more windings that is configured to provide an output signal indicating the volume of the body part of the subject and/or changes in the volume of the body part; and a processing unit that is configured to determine the blood pressure of the subject from the measurements of the pressure in the cuff and the measurements of the volume of the body part and/or the changes in the volume of the body part. A corresponding method claim is also provided.

10 Claims, 6 Drawing Sheets

(51) Int. Cl.
    *A61B 5/107*    (2006.01)
    *A61B 5/0295*   (2006.01)
    *A61B 5/00*     (2006.01)

(52) U.S. Cl.
    CPC ........ *A61B 5/02233* (2013.01); *A61B 5/1073* (2013.01); *A61B 5/6831* (2013.01); *A61B 2562/0223* (2013.01); *A61B 2562/0247* (2013.01)

(56) References Cited

U.S. PATENT DOCUMENTS

| | | |
|---|---|---|
| 2002/0082505 A1 | 6/2002 | Oser |
| 2004/0044290 A1 | 3/2004 | Ward |
| 2009/0306524 A1 | 12/2009 | Muhlsteff |
| 2010/0094140 A1 | 4/2010 | Pranevicius |
| 2011/0087115 A1* | 4/2011 | Sackner ............... A61B 5/0022 600/484 |
| 2014/0296749 A1 | 10/2014 | Reid |
| 2017/0238824 A1 | 8/2017 | Woerlee |

OTHER PUBLICATIONS

Phillip Andrew Shaltis, "A Wearable Blood Pressure Sensor Using Oscillometric Photoplethysmography and Micro Accelerometers", Massachusetts Institute of Technology, 2007.

* cited by examiner

BLOOD PRESSURE MONITOR

CROSS REFERENCE TO RELATED APPLICATIONS

This application is the U.S. National Phase application under 35 U.S.C. § 371 of International Application No. PCT/EP2017/056607, filed Mar. 21, 2017, published as WO 2017/162616 on Sep. 28, 2017, which claims the benefit of European Patent Application Number 16161953.1 filed Mar. 23, 2016. These applications are hereby incorporated by reference herein.

FIELD OF THE INVENTION

The invention relates to a method and blood pressure monitor for measuring the blood pressure of a subject.

BACKGROUND OF THE INVENTION

Arterial blood pressure (BP) is one of the most important vital signs and is widely used in clinical practice. Non-invasive blood pressure (NIBP) is measured by slowly varying the pressure in a cuff that is wrapped around the upper arm and either by measuring the cuff pressure when particular sounds are detected distal from the cuff (auscultatory method, Korotkoff sounds) or by analysis of pressure pulsations in the cuff (oscillatory measurement).

The "gold standard" for cuff based NIBP measurements is the auscultatory method, despite deviations with invasive BP in the order of 10 to 20 mmHg. The oscillatory method on the other hand is easily automated and as a result is widely used. The oscillatory blood pressure method itself has not significantly changed since the 19th century. As described above, an inflatable cuff is placed around the arm of a subject and inflated until the pressure in the cuff is higher than the pressure in the underlying arteries. At this point, the arteries are occluded and collapse and no blood flows. Once this point is reached, the pressure in the cuff is slowly decreased and at the point where the cuff pressure is equal to the pressure in the arteries, the arteries open again and blood begins to pulse through. With each pulse, the arteries temporarily expand and this expansion applies a counter pressure to the cuff, changing the pressure measured inside it. The pressure profile in the cuff is measured and the amplitudes of different oscillations along the profile are used to calculate the systolic and diastolic blood pressures.

Oscillatory blood pressure measurements made in this way can have large errors of the order of tens of mmHgs, particularly at low and high blood pressures.

It is known that the cuff based method is subject to systematic errors due to: (i) the pressure drop over the (visco-elastic) vessel wall; (ii) pressure transmission over soft tissue which means that some of the pressure changes due to volume changes in the arteries are absorbed by surrounding soft tissue rather than being transmitted to the cuff; (iii) size of the cuff (the accuracy of the cuff measurement is improved if the cuff is sized to the limb); (iv) the mechanical properties of the arm; (v) size of the arm (larger arms may suffer from larger pressure transmission); (vi) cuff placement; and (vii) the pressure dependent compliance of the cuff, i.e. how well volume changes in the arm are translated to pressure changes in the cuff.

The state of the art NIBP technology combines actuator (i.e. pressure application) and sensor functions in a single element (i.e. the cuff) and suffers from high non-linearity of the sensor transfer function and therefore very small sensitivity of the sensor at low cuff pressures. It is often not easy to separate the small pressure oscillations from the large and rapidly changing base line signal (i.e. the decreasing cuff pressure) and as noted above, the signal to noise is poor. This causes errors in determination of envelope pressures and subsequent blood pressure estimation.

Furthermore the signals depend strongly on cuff size, arm size and changes in arm size during cuff inflation. These factors pose particular challenges when trying to measure the blood pressure of neonates, or at the other end of the scale, people with high Body Mass Index (BMI).

For continuous NIBP measurements, such as volume clamp blood pressure measurements, the cuff cannot be used as a pulsation sensor and therefore a second sensor is needed. In this case photoplethysmography (PPG) sensors are used to estimate arterial volume pulsations. PPG signal to noise is low and PPG suffers from low signal quality when blood flow centralization occurs (i.e. when the measurement is needed most). Furthermore the relation between vessel volume and the PPG signal is not linear and has many confounding dependencies with other parameters (venous blood, low oxygenation, tissue absorption). The PPG signal is also very sensitive to the placement of the sensor relative to major arteries.

SUMMARY OF THE INVENTION

It is an aim of the present invention to avoid or reduce some of these sources of error, particularly at low cuff pressures.

According to a first aspect, there is provided a blood pressure monitor for use in measuring the blood pressure of a subject, the blood pressure monitor comprising a cuff that is configured to be placed around a body part of the subject and inflated to apply pressure to the body part; a pressure sensor that is configured to provide measurements of the pressure in the cuff; a plethysmography sensor comprising a coil having one or more windings that is configured to provide an output signal indicating the volume of the body part of the subject and/or changes in the volume of the body part; and a processing unit that is configured to determine the blood pressure of the subject from the measurements of the pressure in the cuff and the output signal indicating the volume of the body part of the subject and/or the changes in the volume of the body part.

In some embodiments, the coil is configured to be placed around the body part of the subject such that the body part lies within the one or more windings and changes in the volume of the body part of the subject change the cross-sectional area of the windings.

In some embodiments, the plethysmography sensor is integrated into the cuff such that the output signal of the plethysmography sensor is linearly proportional to the cross-sectional area of the cuff. In alternative embodiments, the plethysmography sensor is configured to be placed around the body part beneath the cuff such that the output signal of the plethysmography sensor is linearly proportional to the cross-sectional area of the cuff. In these embodiments, the plethysmography sensor can be part of a stretchable band that is configured to be placed around the body part. In these embodiments, the wire in the coil can be arranged in the stretchable band to enable the windings of the coil to be stretched or compressed as the volume of the body part changes.

In some embodiments, the wire in the coil is formed from a conductive stretchable material to enable the windings of the coil to be stretched or compressed as the volume of the body part changes.

In some embodiments, the output signal of the plethysmography sensor comprises a measurement of the inductance of the coil.

In some embodiments, the coil is part of a resonance circuit of an oscillator, and wherein the output signal of the plethysmography sensor comprises a measurement of a frequency of the oscillator.

In some embodiments, the wire in the coil is formed from a conductive stretchable material or a piezoelectric material, and wherein the output signal of the plethysmography sensor comprises a measurement of the resistance of the coil.

In alternative embodiments, the plethysmography sensor comprises two or more coils each having one or more windings, wherein the two or more coils are configured to be placed around the body part of the subject such that changes in the volume of the body part of the subject change the distance between the two or more coils, and wherein the output signal of the plethysmography sensor comprises a measurement of the mutual inductance of the coils. In these embodiments, the plethysmography sensor can be integrated into the cuff. Alternatively, the plethysmography sensor can be configured to be placed around the body part beneath the cuff. In some embodiments, the plethysmography sensor is part of a stretchable band that is configured to be placed around the body part.

In another alternative, the plethysmography sensor comprises a first coil and a second coil, each coil having one or more windings, wherein the first coil is located on an inner surface of the cuff and the second coil is located opposite to the first coil on an outer surface of the cuff such that changes in the volume of the body part of the subject change the distance between the first coil and the second coil, and wherein the output of the plethysmography sensor comprises a measurement of the mutual inductance of the first coil and the second coil.

In some embodiments, the processing unit is configured to analyze the output signal from the plethysmography sensor and to control the pressure in the cuff such that the output signal from the plethysmography sensor is equal to or within a specified tolerance level of a set point.

In some embodiments, the blood pressure monitor further comprises a pump for inflating the cuff.

According to a second aspect, there is provided a method of measuring the blood pressure of a subject, the method comprising placing a cuff around a body part of the subject and inflating the cuff to apply pressure to the body part; measuring the pressure in the cuff using a pressure sensor; measuring the volume of the body part of the subject and/or changes in the volume of the body part due to arterial pulsations using a plethysmography sensor comprising a coil having one or more windings; and determining the blood pressure of the subject from the measurements of the pressure in the cuff and the measurements of the volume of the body part and/or the changes in the volume of the body part due to arterial pulsations.

In some embodiments, the method further comprises the step of placing the plethysmography sensor around the body part of the subject such that the body part lies within the one or more windings and changes in the volume of the body part of the subject change the cross-sectional area of the windings.

In some embodiments, the plethysmography sensor is integrated into the cuff such that the output signal of the plethysmography sensor is linearly proportional to the cross-sectional area of the cuff. In alternative embodiments, the method further comprises the step of placing the plethysmography sensor around the body part beneath the cuff such that the output signal of the plethysmography sensor is linearly proportional to the cross-sectional area of the cuff. In these embodiments, the plethysmography sensor can be part of a stretchable band that is placed around the body part. In these embodiments, the wire in the coil can be arranged in the stretchable band to enable the windings of the coil to be stretched or compressed as the volume of the body part changes.

In some embodiments, the wire in the coil is formed from a conductive stretchable material to enable the windings of the coil to be stretched or compressed as the volume of the body part changes.

In some embodiments, the step of measuring the volume of the body part of the subject and/or changes in the volume of the body part the subject comprises measuring the inductance of the coil.

In some embodiments, the coil is part of a resonance circuit of an oscillator, and wherein the step of measuring the volume of the body part of the subject and/or changes in the volume of the body part the subject comprises measuring a frequency of the oscillator.

In some embodiments, the wire in the coil is formed from a conductive stretchable material or a piezoelectric material, and wherein the step of measuring the volume of the body part of the subject and/or changes in the volume of the body part the subject comprises measuring resistance of the coil.

In alternative embodiments, the plethysmography sensor comprises two or more coils each having one or more windings, wherein the method further comprises the step of placing the two or more coils around the body part of the subject such that changes in the volume of the body part of the subject change the distance between the two or more coils, and wherein the step of measuring the volume of the body part of the subject and/or changes in the volume of the body part the subject comprises measuring the mutual inductance of the coils. In these embodiments, the plethysmography sensor can be integrated into the cuff. Alternatively, the plethysmography sensor can be placed around the body part beneath the cuff. In some embodiments, the plethysmography sensor is part of a stretchable band that is placed around the body part.

In another alternative, the plethysmography sensor comprises a first coil and a second coil, each coil having one or more windings, wherein the first coil is located on an inner surface of the cuff and the second coil is located opposite to the first coil on an outer surface of the cuff such that changes in the volume of the body part of the subject change the distance between the first coil and the second coil, and wherein the step of measuring the volume of the body part of the subject and/or changes in the volume of the body part the subject comprises measuring the mutual inductance of the first coil and the second coil.

In some embodiments, the method further comprises the steps of analyzing the output signal from the plethysmography sensor and controlling the pressure in the cuff such that the output signal from the plethysmography sensor is equal to or within a specified tolerance level of a set point.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

As described above, traditional oscillatory blood pressure measurements can be inaccurate because the change in volume, dV, of the arm due to arterial pulsations is not linearly proportional to the pressure change, dP, measured in the cuff. This non-linearity is characterized by the cuff compliance C, defined as $$C = dV/dP \tag{1}$$

The cuff compliance links the change in volume dV of the arm to the resulting pressure change dP measured in the cuff. A high cuff compliance may reflect that changes in arm volume do not result in expected changes in cuff pressure, for example, due to factors such as the material of the cuff deforming such that the pressure from the change in arterial volume is not fully transferred to the cuff pressure. Also, a high cuff compliance value may indicate that the expansion of the arm is taken up laterally rather than radially into the cuff.

The invention aims to improve measurements of blood pressure by providing a plethysmography sensor that is separate to the cuff pressure sensor for measuring the volume of a body part and/or the change in volume of the body part due to arterial pulsations. This allows for body part (e.g. arm) volume and arterial volume pulsations to be measured with high precision and low distortion for a wide range of cuff pressures. The use of a separate plethysmography sensor removes the non-linear dependence of the cuff pressure on the change in volume, since volume or changes in volume can be directly measured. The plethysmography sensor that has an output signal that is preferably linearly proportional to the cross sectional area or volume of the body part. In addition, the plethysmography sensor embodiments described herein do not require precise placement on the subject and therefore mitigate some of the disadvantages associated with PPG sensors noted above. A blood pressure monitor including a plethysmography sensor can be used for both intermittent and continuous blood pressure measurements and/or blood pressure tracking.

Figure 1:
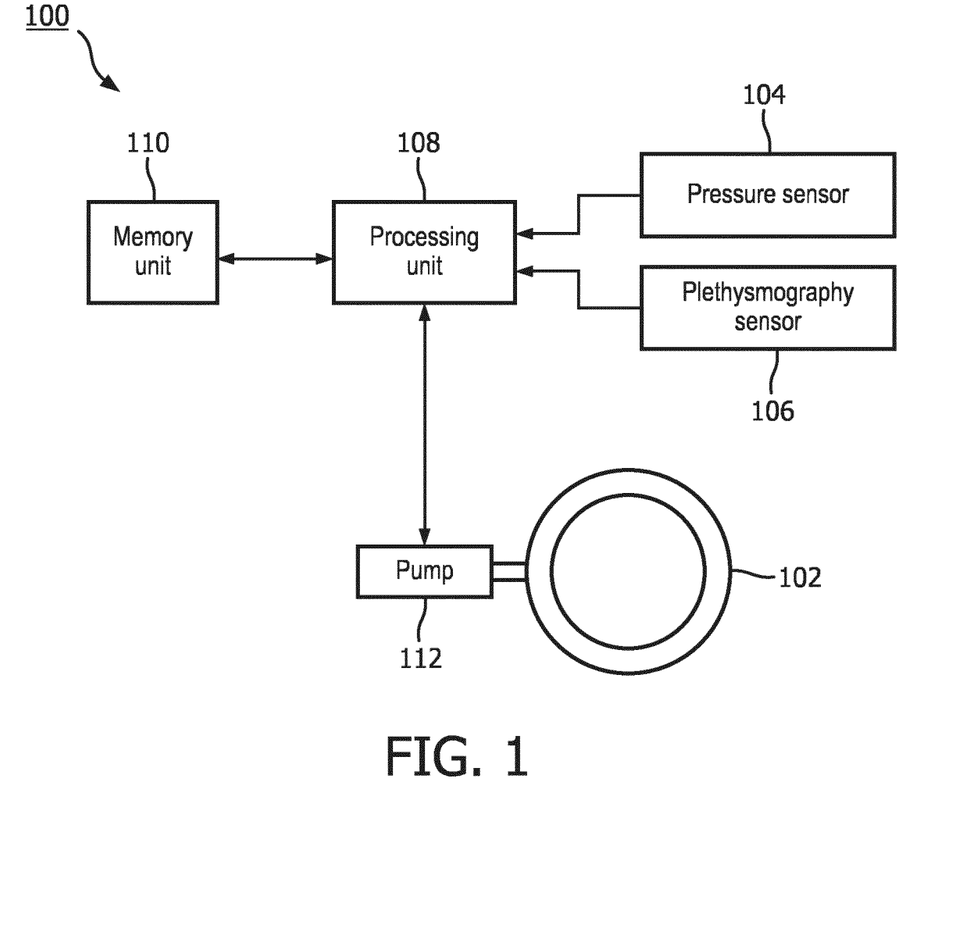
FIG. 1 is a block diagram of an apparatus according to an embodiment of the invention.

FIG. 1 shows a block diagram of an apparatus according to an exemplary embodiment of the invention that can be used to determine the blood pressure of a subject. The apparatus can be any type of device that is able to measure the blood pressure of a subject automatically (e.g. without an operator being present with the subject) or manually (e.g. that requires the presence of an operator, such as a healthcare professional). The apparatus is a cuff-based device that operates to measure the blood pressure of the subject using the auscultatory or oscillometric methods. Alternatively the apparatus can be a cuff-based device that uses the volume-clamp method to measure blood pressure.

The apparatus 100, e.g. a blood pressure monitor, comprises a cuff 102, a pressure sensor 104, a plethysmography sensor 106, a processing unit 108, a memory unit 110 and a pump 112.

The cuff 102 is configured to be placed around a limb (e.g. arm), digit (e.g. finger) or other body part of a subject and inflated by the pump 112 to apply pressure to the body part. The pump 112 is for inflating the cuff 102 to a desired pressure or at a desired rate, and the pressure sensor 106 is configured to provide pressure measurements of the pressure inside the cuff 102. The pump 112 may also be configured to deflate the cuff 102 to a desired pressure or at a desired rate and/or the apparatus 100 can comprise a valve that can be controlled (i.e. opened) to deflate the cuff 102. The cuff 102 may be formed as a strip that can be wrapped around the body part and held by place by a fastening, for example a hook and loop-type fastening, or it may be formed as a loop through which the body part can be placed and the cuff slid into the required position.

In accordance with the invention, the plethysmography sensor 106 comprises a coil having one or more windings and is configured to provide an output signal indicating the volume of the body part of the subject and/or changes in the volume of the body part. It will be appreciated that the output signal from the plethysmography sensor 106 may not itself directly indicate the volume of the body part or changes in the volume of the body part, but instead the output signal may take a value that is dependent on the volume of the body part or changes in the body part. For example, in some embodiments the inductance of the coil is dependent on the cross-sectional area of the coil (which is the cross-sectional area of the body part), and the coil can be incorporated in a resonance circuit of an oscillator so that the frequency of the oscillator provides the indication of volume or changes in volume of the body part. A coil-based plethysmography sensor 106 has an advantage that the output of the sensor 106 is generally linearly proportional to the cross sectional area or volume of the body part, regardless of the pressure in the cuff 102.

The processing unit 108 is configured to receive the pressure measurements from the pressure sensor 104 and volume measurements from the plethysmography sensor 106 and determine the blood pressure of the subject from the measurements of the pressure in the cuff 102, and the measurements of the volume of the body part and/or the changes in the volume of the body part. Briefly, the processing unit 108 determines the blood pressure of the subject (e.g. diastolic and/or systolic blood pressure) from an envelope of the volume changes in a similar way to conventional oscillometric techniques that determine blood pressure from the envelope of a pressure signal. It will be appreciated that an algorithm to determine values may be adapted, i.e. different values of the normalized volume envelope are used for determining diastolic and systolic pressure.

The volume measurement signal consists of a slowly varying part (which is related to the volume of the body part (arm, wrist, finger, leg, etc.) and an oscillating/pulsating part (which is due to arterial volume oscillations). The volume signal can be high pass or band pass filtered such that oscillations/pulsations in volume (due to arterial pulsations) can be extracted from the signal. The volume oscillations depend on transmural pressure (i.e. arterial pressure—cuff pressure). Peak values depend on transmural pressure in a similar way to a reference oscillometric method, but are not influenced by cuff compliance. Furthermore the dependence of the non-oscillating part of the volume signal is less strong than that of the reference method, hence a cleaner signal can be obtained with simpler signal processing. A curve of volume oscillation amplitude versus cuff pressure can be used to extract the systolic, mean and/or diastolic blood pressure since the cuff pressure (horizontal axis) is related to the blood pressure.

The processing unit 108 can be implemented in numerous ways, with software and/or hardware, to perform the various functions required. The processing unit 108 may comprise one or more microprocessors that may be programmed using software to perform the required functions. The processing unit 108 may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, the processing unit 108 may be associated with one or more storage media (shown as memory unit 110 in FIG. 1) such as volatile and non-volatile computer memory such as RAM, PROM, EPROM, and EEPROM. The apparatus 100 can also comprise a memory unit 110 that can be used for storing program code that can be executed by the processing unit 108 to perform the method described herein. The memory unit 110 can also be used to store signals and measurements made or obtained by the pressure sensor 104 and/or plethysmography sensor 106, and/or measurements of the blood pressure determined by the apparatus 100.

In some embodiments the processing unit 108 and the memory unit 110 are part of the same unit as the cuff 102, the pressure sensor 104, the plethysmography sensor 106 and the pump 112. In other embodiments, the processing unit 108 and the memory unit 110 are in a separate unit to the cuff 102, the pressure sensor 104, the plethysmography sensor 106 and the pump 112. In these embodiments the processing unit 108 is configured to obtain measurements of the cuff pressure and volume of the body part of the subject as measured by the pressure sensor 104 and plethysmography sensor 106 respectively, for example via a wireless or wired connection between the processing unit 108 and the sensors 104, 106. Therefore, in these embodiments, the apparatus 100 may further comprise a transmitter module and receiver module or transceiver modules that are configured to send the measurements from the sensors 104, 106 to the processing unit 108 for processing.

The measurements from the pressure sensor 104 and the plethysmography sensor 106 can be processed by the processing unit 108 as the measurements are obtained (e.g. in real-time or near real-time), or they can be stored in the memory unit 110 and the processing unit 108 can retrieve the previously-obtained measurements from the memory unit 110 and process them at a later time.

In some embodiments the processing unit 108 may be part of or in the form of a smart phone or other general purpose computing device that can comprise, be connected to or otherwise receive a measurement signal from the pressure sensor 104 and plethysmography sensor 106.

It will be appreciated that FIG. 1 only shows the components required to illustrate this aspect of the invention, and in a practical implementation the apparatus 100 may comprise additional components to those shown. For example, the apparatus 100 may comprise a battery or other power supply for powering the apparatus 100 or means for connecting the apparatus 100 to a mains power supply. The apparatus 100 may also comprise a communication module for enabling the sensor measurements and/or the measurement of the blood pressure to be communicated to a base unit for the apparatus 100 or a remote computer. The apparatus 100 may also comprise at least one user interface component that is for use in providing the subject or other user of the apparatus 100 (for example a family member or healthcare provider) with information resulting from the blood pressure measurement. Alternatively or in addition, the user interface component can provide an indication of how the blood pressure measurement has changed over time (e.g. relative to an immediately preceding or other earlier measure). The user interface component can comprise any component that is suitable for providing the above information, and can be, for example, any one or more of a display screen or other visual indicator, a speaker, one or more lights, and a component for providing tactile feedback (e.g. a vibration function).

Figure 2:
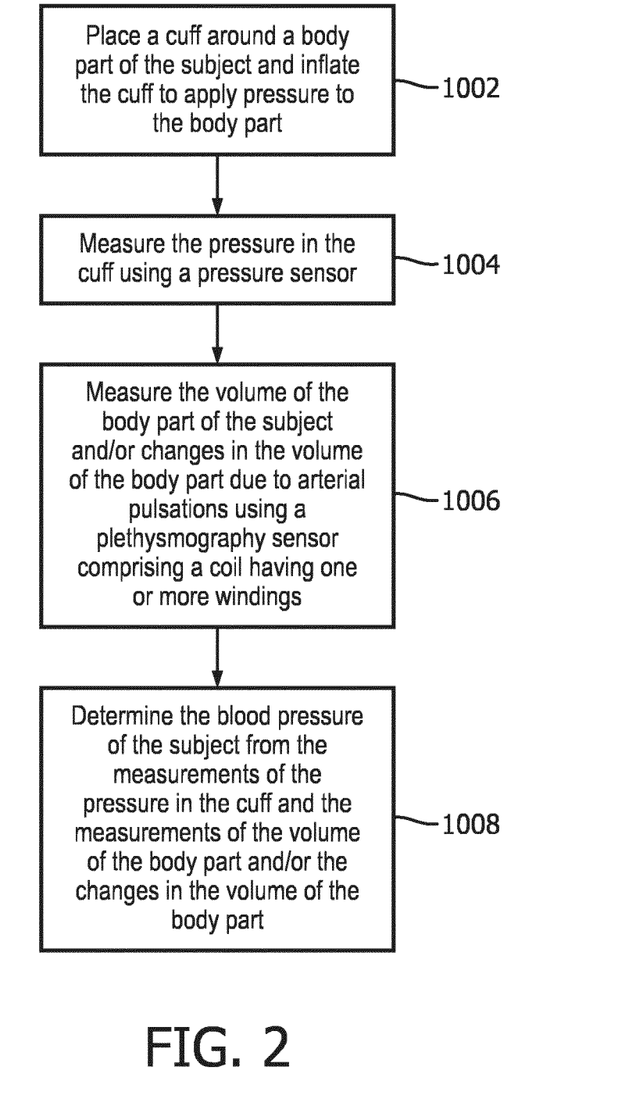
FIG. 2 is a flow chart illustrating a method according to an embodiment of the invention

FIG. 2 illustrates a method of measuring the blood pressure of a subject according to an embodiment of the invention. The method comprises placing a cuff 102 around a body part of the subject and inflating the cuff 102 to apply pressure to the body part (step 1002). In subsequent steps, the pressure in the cuff 102 is measured using a pressure sensor 104 (step 1004) and the volume of the body part of the subject and/or changes in the volume of the body part due to arterial pulsations are measured using a plethysmography sensor 106 comprising a coil having one or more windings (step 1006). Steps 1004 and 1006 can be performed while the pressure in the cuff 102 is being increased, decreased or maintained at a generally constant level, depending on the type of blood pressure measurement being made.

The method then comprises determining the blood pressure of the subject from the measurements of the pressure in the cuff 102 and the measurements of the volume of the body part and/or the changes in the volume of the body part due to arterial pulsations (step 1008).

Various exemplary embodiments of the plethysmography sensor 106 that can be used in the apparatus 100 and/or the method of FIG. 2 are presented below.

As noted above, the plethysmography sensor 106 comprises a coil having one or more windings. A coil type inductor has a self-inductance, L, of:

$$L = \mu_0 \frac{A \cdot N^2}{l} \quad (2)$$

where $\mu_0$ is the permeability of free space, A is the area of the coil, N is the number of windings and l is the length of the coil. L is proportional to the square of the number of windings, N, the area, A, of the coil and inversely proportional to the length l. Hence, L is linearly proportional to A. Changes dA due to small oscillations around A can therefore be measured with high precision and without distortion by measuring the inductance of the coil.

Thus, in some embodiments, a coil can be used to measure the volume and/or changes in volume of a subject's limb or other body part by placing the coil around the body part of the subject such that the body part lies within the one or more windings. In this way, if the coil is in contact with the body part, changes in the volume of the body part of the subject will change the cross-sectional area A of the windings. For example, as the volume of the body part increases, this will cause a corresponding increase in the cross sectional area A of the coil. Likewise, as the volume of the body part decreases, this will cause a corresponding decrease in the cross sectional area of the coil. Thus, in these embodiments, measuring the inductance of the coil can provide measurements of the volume or changes in volume of the body part.

Figure 3:
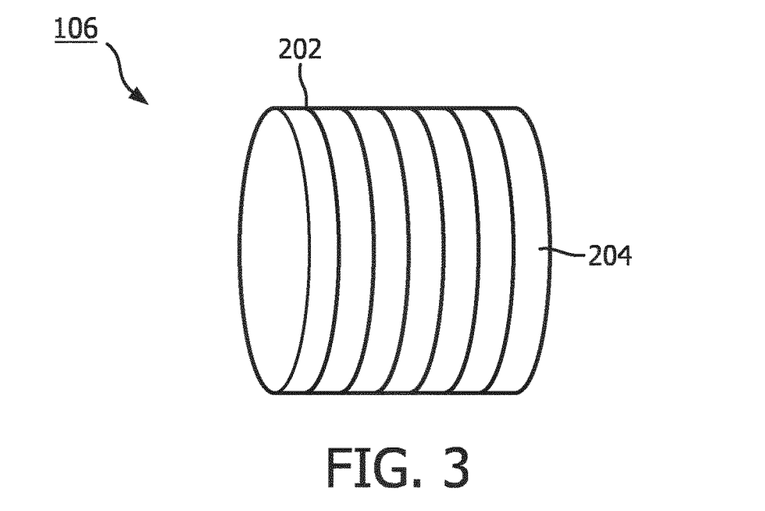
FIG. 3 is a schematic diagram of a plethysmography sensor according to an embodiment of the invention.

A plethysmography sensor 106 according an exemplary embodiment is shown in FIG. 3. In some embodiments, the coil 202 forming the plethysmography sensor 106 is part of (e.g. attached to or integral with) a stretchable band 204 that is configured to be placed around the body part. In some embodiments, stretchable band 204 can be pulled over the subject's limb like a sleeve. In other embodiments, stretchable band 204 is a strip of material that can be wrapped around the body part and the ends held together by a suitable fastening, e.g. a hook-and-loop-type fastening.

Plethysmography sensor 106 comprises N windings (where N is any desired value equal to or greater than 1) in coil 202 that are arranged on the stretchable band so that in use, the windings of the coil can be stretched or compressed as the volume of the underlying body part changes. In the embodiment shown in FIG. 3, the coil 202 has six windings (i.e. N=6). In some embodiments the wires forming the coil 202 can be arranged in a zig-zag pattern around the stretchable band 204 or the wires can have a spring shape so that the cross-section of the coil 202 can stretch (i.e. expand) as the stretchable band 204 is stretched. In other embodiments, the wire forming the coil 202 is formed of a conductive stretchable material so that the wires and thus the cross-section of the coil 202 can stretch and contract with changes in the volume of the body part. An example of a suitable conductive stretchable material is conductive rubber.

The stretchable band 204 can be made of any suitable type of stretchable material, such as elastic, rubber, plastic or a textile. In some embodiments, the plethysmography sensor 106 (including stretchable band 204) is integrated in the cuff 102. In alternative embodiments, plethysmography sensor 106 is separate from cuff 102. In these embodiments, in use, the stretchable band 204 comprising the coil 202 is first placed around, or pulled up the body part (e.g. arm). The cuff 102 is then positioned over the stretchable band 204 so that inflation of the cuff 102 applies pressure to the stretchable band 204 and the underlying body part. Since the band is stretchable, it follows the outer surface of the body part (whether the cuff 102 is inflated or not), and thus variations in the cross section and volume of the body part (e.g. due to brachial artery pulsations) are reflected by equivalent variations in the cross section and volume of the stretchable band 204 and coil 202.

It will be appreciated that a traditional cuff based measurement of the blood pressure can be made using the cuff surrounding the plethysmography sensor 106, and thus the plethysmography sensor 106 can be calibrated against the traditional cuff based measurement. For example, the cuff pressure can be recorded and the cuff pressure measurements filtered and processed to obtain the cuff pressure envelope in the usual manner and blood pressure measurements derived therefrom. The plethysmography sensor 106 will not cause appreciable deformation of the pressure envelope. In this way the volume envelope-derived blood pressure can be calibrated against a conventional oscillometric measurement. Alternatively, a similar calibration can be performed using an auscultatory-based reference measurement.

Figure 4A:
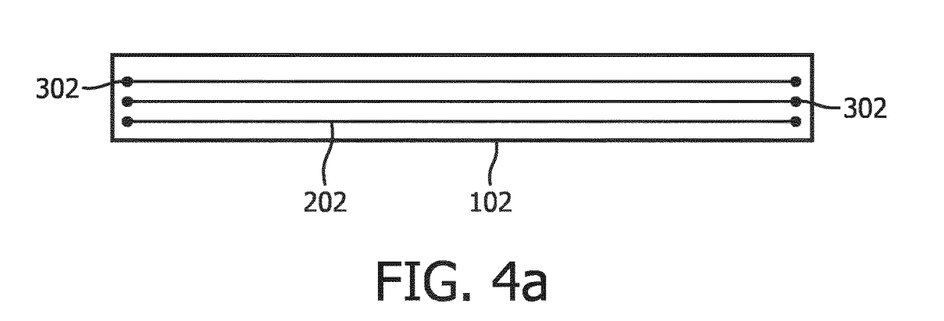
FIGS. 4a and 4b show a blood pressure cuff and plethysmography sensor according to an embodiment of the invention.
Figure 4B:
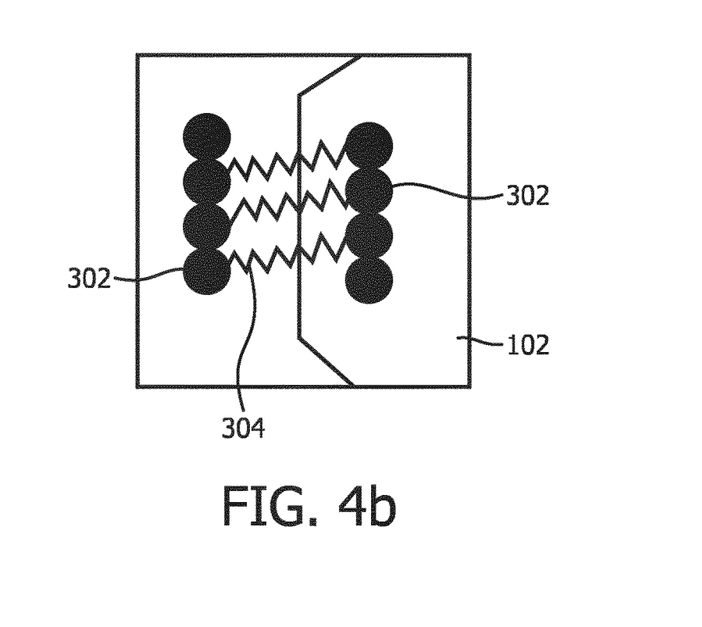

FIGS. 4a and 4b show an embodiment of the invention where the coil 202 of the plethysmography sensor 106 is integrated into cuff 102. As shown in FIG. 4a, in this embodiment the cuff 102 is formed as a strip that is to be wrapped around the body part (e.g. arm or finger) and then fastened or held together, for example using a hook-and-loop type fastening. One of the challenges of integrating windings directly into a cuff of this type is that the coil windings have to be continuous loops. The embodiment shown in FIG. 4a therefore comprises electrical connecting parts 302 that are used to electrically connect the ends of the coil wires 202 together when the cuff 102 is wrapped around the subject's body part. In some embodiments, the connecting parts 302 comprise snap buttons or fittings that each connect with a corresponding snap button or fitting on the other side of the cuff, or flexible wiring 304 as shown in FIG. 4b, that can be fed through the cuff 102 to electrically connect the connecting parts 302. It will be appreciated that in the embodiments above where the coil 202 is part of a stretchable band 204 that is formed as a strip of material that is to be wrapped around the body part, the coil and stretchable band can comprise connecting parts 302 for electrically connecting the coil wires in a similar way to the cuff embodiments described above.

As noted above, in the embodiments above where the windings of the coil 202 are placed around the body part, the volume of the body part or changes in the volume of the body part can be obtained by measuring the inductance of the coil 202.

The change in the cross sectional area of an arm of radius, r, 2 cm to 5 cm due to arterial volume oscillations during inflation of the cuff is of the order of 0.1% to 0.8% with a corresponding change in volume (dV) on the order of 1 ml. This corresponds to a change in radius of 0.05% to 0.4%. A change in radius of this magnitude can be measured using inductance measurements if the inductance measurements have a precision better than 0.01%. As another example, the inductance L for a typical arm with a radius, r, of 5 cm and a length of the coil of 10 cm and 10 windings (i.e. N=10) is obtained from equation (2) above as L~10 µH. High precision is therefore required to measure inductance and/or changes of the magnitude of L. Exemplary techniques for measuring the inductance of the coil 202 are described below.

In some preferred embodiments, to achieve the required accuracy, the coil 202 of the plethysmography sensor 106 is incorporated in the resonance circuit of an oscillator and the frequency of the oscillator is measured. In this embodiment, the output signal of the plethysmography sensor 106 can comprise a measurement of the frequency of the oscillator. The frequency of the oscillator can be measured with high precision, for example using a counter or with an accurate time measurement.

Figure 5:
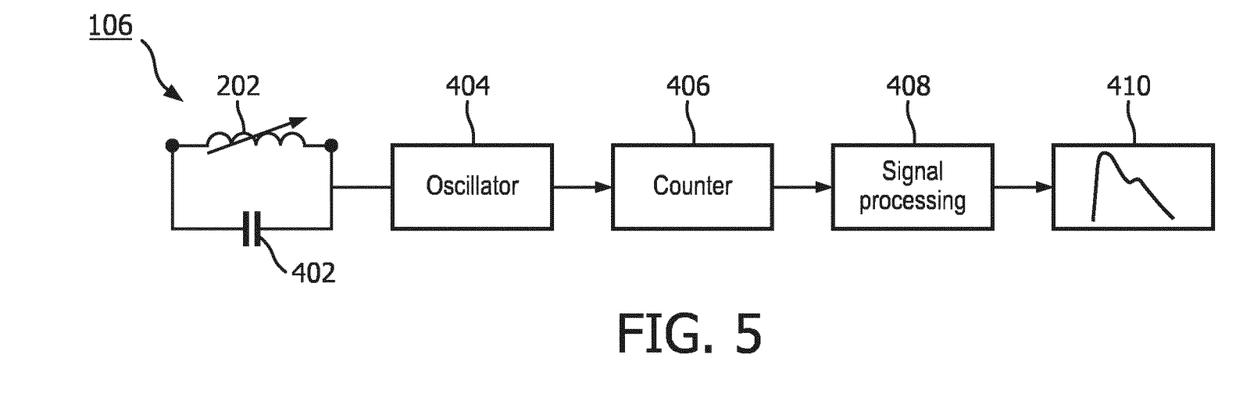
FIG. 5 shows an example of a plethysmography sensor according to an embodiment.

A functional diagram for an embodiment of a plethysmography sensor 106 that comprises a coil 202 incorporated into the resonance circuit of an LC oscillator is shown in FIG. 5. An exemplary type of LC oscillator that can be used is a Colpitts oscillator. FIG. 5 shows the coil 202 (with inductance L) of the plethysmography sensor 106 connected in parallel with a capacitor 402 (with capacitance C), which determine the oscillation frequency of an oscillator 404. The resonant frequency of oscillator 404 is measured by counter 406. In particular, the counter 406 counts the number of events per unit time, e.g. where the signal passes a certain threshold value, and thus the number of counts per unit of time indicates the frequency of the oscillator 404. Signal processing 408 is applied to the output of the counter to produce measurements of the resonant frequency over time, as shown in block 410. The signal processing unit 408 converts the output of the counter 406 to a frequency, the frequency to an inductance L, and the inductance L to a volume signal. Noise and artefacts can be removed at one or more stages of the signal processing. Digital filtering and other digital signal processing (DSP) techniques can be used in the counter 406 to improve accuracy.

Instead of using counter 406, a time-based measurement could be used instead. The time-based measurement may consist of fast Fourier analysis of a digital time series. Alternatively step pulses can be applied, and the ringing signal can be measured by accurate time based sampling. The frequency of the oscillator 402 can be extracted from the ringing signal. In other alternatives, frequency sweeps or an LCR (inductance, capacitance and resistance) meter can be used to measure the inductance For an LC resonator with L equal to 10 μH and a capacitance C of 10 nF the resonant frequency is approximately 500 kHz, which can be measured with a high level of accuracy. It will be noted that the resonant frequency is proportional to $1/\sqrt{A}$ i.e. proportional to $1/r$ (where r is the radius of the body part), and thus changes in the cross-sectional area and thus volume of the body part (since the length of the coil is known) can be derived from the measured resonant frequency with very high accuracy.

In some embodiments, the oscillator 404 is integrated in the cuff 304 to reduce the influence of parasitic elements. The capacitance of wires can be appreciable and this also holds for inductance (nF/mm). Therefore it is preferable for the effect of parasitic elements on the resonant frequency not to be neglected. Also with motion of the subject the values would change leading to false readings. It is therefore useful to reduce the values of these parasitic elements and reduce the impact of motion on the volume measurements. This reduction can be achieved by locating the electronics (e.g. the oscillator 404) close to the coil 202, i.e. on the cuff 102.

In an alternative embodiment, amplitude modulation, AM, or frequency modulation, FM, demodulation techniques can be used either in the analog or digital domain to measure the resonance frequency of the oscillator 404.

Figure 6:
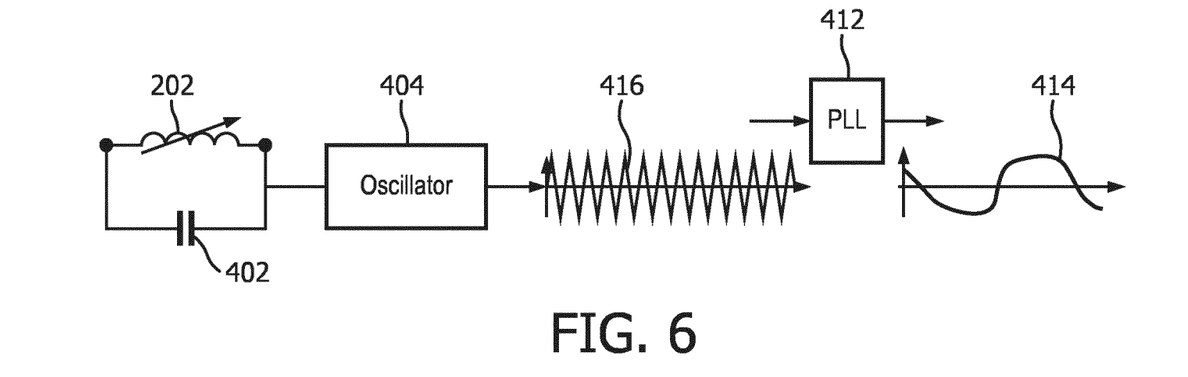
FIG. 6 shows an example of a plethysmography sensor according to another embodiment.

FIG. 6 is a functional diagram of an exemplary embodiment of the invention in which FM demodulation techniques are used to measure the resonant frequency of an LC oscillator formed from the coil 202 of the plethysmography sensor 106 and a capacitor 402. The FM signal 416 from the oscillator 404 is provided to a phase-locked loop (PLL) 412 which outputs a demodulated voltage, shown as signal 414. The output of the phase-locked loop 412 can be processed, for example filtered and/or a DC offset removed, and the signal 414 used to determine the volume or changes in volume of the body part. As is known, a PLL is a closed loop control system that generates an output signal with a phase and frequency that is identical to the input signal, and therefore a PLL can be used to track the frequency of a signal. A PLL 412 can comprise a variable frequency oscillator (VCO) and a phase detector (which is feedback based). The phase detector controls the VCO such that the input and output signals are matched. The phase detector generates an output signal that can be low-pass filtered and then input to the VCO. The frequency of the demodulated output signal is the resonance frequency, and since the capacitance is fixed, the inductance can be calculated, and from the inductance the volume signal can be obtained.

Figure 7:
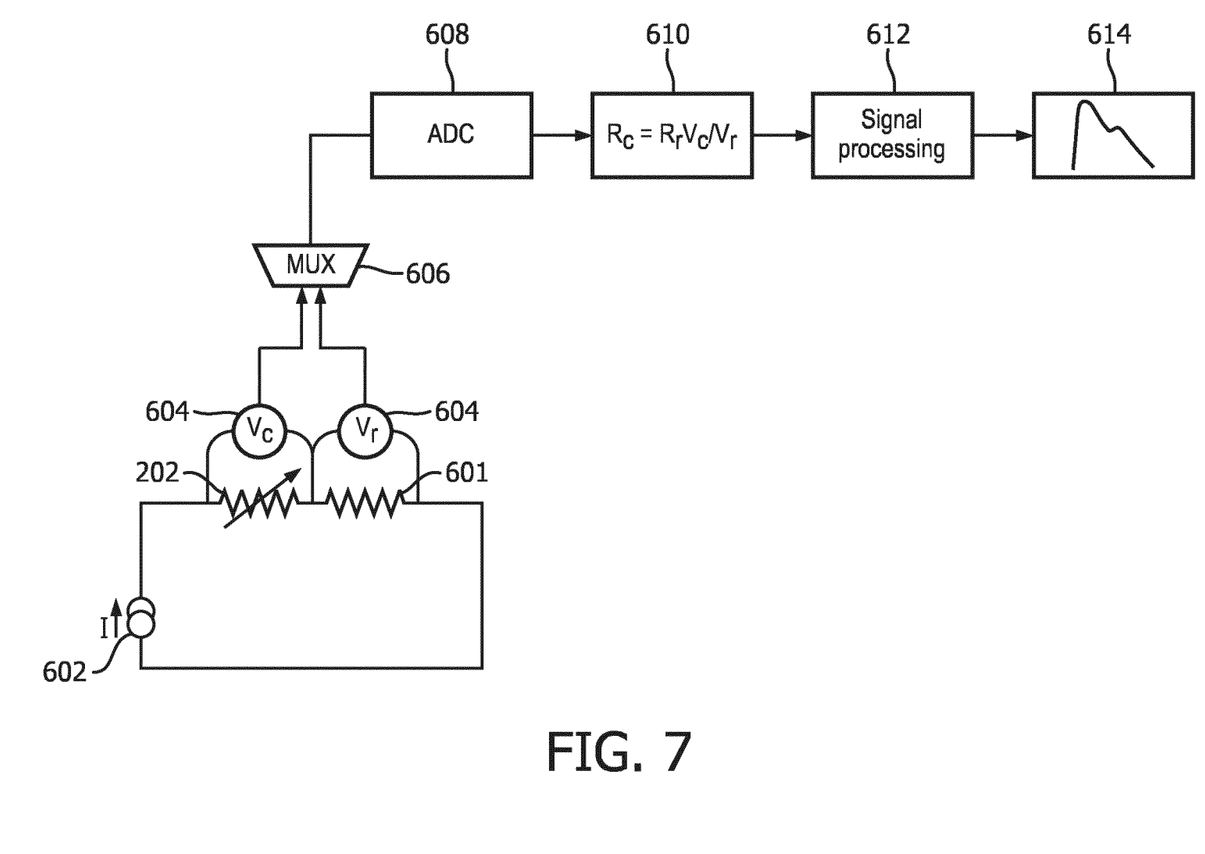
FIG. 7 shows another example of a plethysmography sensor according to an embodiment.

In embodiments where the wires in the coil 202 of the plethysmography sensor 106 are formed from a conductive stretchable material, e.g. conductive rubber, or a material that provides a signal proportional to the stress on the wire (e.g. due to stretching), such as a piezoelectric material, it is possible to measure the volume of the body part or changes in the body part by measuring the resistance of the coil 202. FIG. 7 shows a plethysmography sensor 106 according to an embodiment of the invention where resistance of the coil is measured to provide the plethysmography sensor 106 output signal.

Volume oscillations lead to a small variation in the circumference of the coil/band (given by $2\pi r$, where r is the radius of the coil/body part) which causes a change in the geometry of the wire (both in the length and cross section). The resistance can be measured relatively easily and with high precision which is advantageous for the purpose of measuring volume changes of a body part. For an arm, the estimated change in circumference is between 0.5‰ and 0.5% and hence the precision of the resistance measurement has to be better than 0.01‰.

In this embodiment, the resistance of the coil 202 is measured with high precision using a 4 point method and an alternating current (AC). The 4 point method is well-known to those skilled in the art, and further details are not provided herein.

In this embodiment, the coil 202 is connected in series with a reference resistance 601 and a current source 602. The voltages across the coil 202 (denoted $V_c$) and the reference resistance 601 (denoted $V_r$) are measured by respective volt meters 604. The measurements are fed into multiplexer 606 which switches measurement contacts between the known reference resistor 601 and the coil 202. By comparing the voltages of the reference resistance 601 and coil 202 the unknown resistance value can be determined. The output of the multiplexer 606 is converted into a digital signal by analog-to digital (ADC) converter 608 so that further processing is performed in the digital domain. The resistance of the coil $R_c$ in the plethysmography sensor 106 is then computed at block 610 from the voltage across the coil, $V_c$, the voltage across the reference resistance, $V_r$, and the known resistance of the reference resistance $R_r$ using the relationship:

$$R_c = \frac{V_c}{V_r} R_r \tag{3}$$

The output of block 610 (the value of the resistance of the coil) can be further processed in the analog domain (if An apparatus as claimed in claim 608 is not present or used) or the digital domain (e.g. by filtering, removing a DC offset) to generate a clean resistance signal 614 that can be used to determine the arterial volume pulsation.

Figure 8:
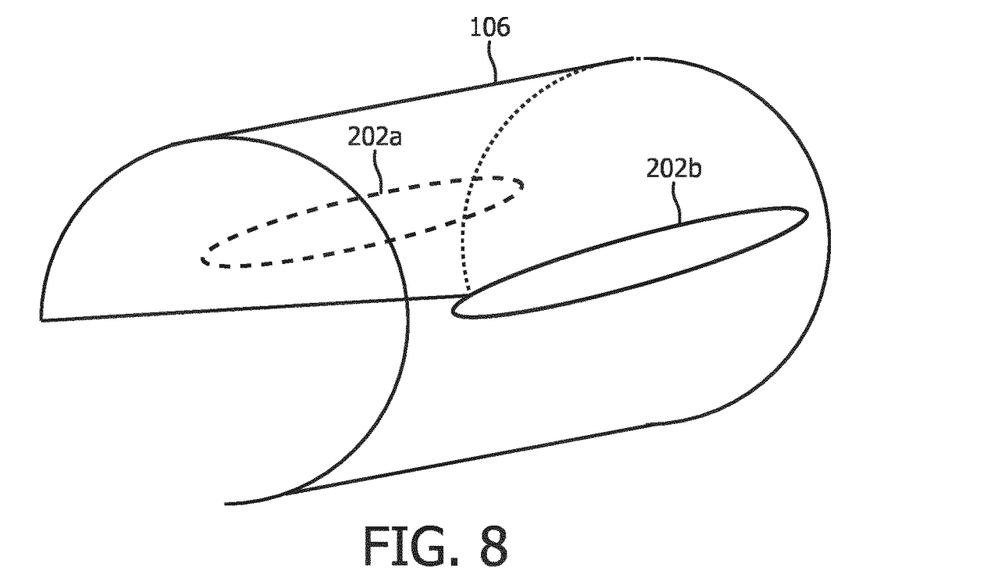
FIG. 8 shows an embodiment of a plethysmography sensor comprising a pair of coils.

In alternative embodiments of the invention, rather than arrange a coil 202 so that the windings go around a body part, the mutual inductance between two or more coils arranged on either side of the body part can be used to measure the volume or volume changes of the body part. In this embodiment, an example of which is shown in FIG. 8, the plethysmography sensor 106 comprises two or more coils, 202a and 202b, each having one or more windings.

Coils 202a and 202b are placed around the body part of the subject such that changes in the volume of the body part of the subject change the distance between the two coils. In some embodiments, the coils are on opposite sides of the body part so that they are separated by a distance equal to twice the radius r of the body part. The coils 202a, 202b are preferably arranged so that they are in the same orientation (i.e. the planes of the coils are parallel) to improve their mutual induction. In this embodiment, the coils 202a and 202b can be integrated into a cuff 102, or provided in a separate band of stretchable material as in the embodiment shown in FIG. 3.

As is known, the density of a magnetic field generated by a current passing through a coil, e.g. coil 202a, is inversely proportional to the cube of the distance, d, from the coil 202a. This magnetic field from coil 202a will induce a voltage in coil 202b. This induced voltage is proportional to the rate of change of the magnetic flux from coil 202a, and thus the induced voltage is sensitive to the distance between the coils, and thus sensitive to the volume of the body part.

When the body part volume increases by dV for a cuff length of 1 the increase in body part radius dr is equal to:

$$dr = \frac{dV/l}{2\pi r} \quad (4)$$

For a 5 cm body part radius this corresponds to an increase in radius dr=0.03 mm. The relative change dr/r for given r and dV is equal to:

$$\frac{dr}{r} = \frac{dV/l}{2\pi r^2} \quad (5)$$

For a 5 cm radius according to the example above, dr/r~0.0006. The relative change in magnetic field dB/B at distance 2r is dB~3dr/r. For 5 cm radius dB/B~0.0018, hence dB/B has to be measured with very high accuracy (<<0.1‰). This can be achieved with various methods. For instance measurement of induced voltage in coil 202b in open condition after a step voltage in coil 202a is an option. Bridge methods can also be used for high accuracy and precision. Finally methods based on resonance frequency can be used.

One of the advantages associated with this embodiment is that the coils do not need to form continuous loops around the circumference of the body part as in the embodiment of FIG. 3. Thus, the coils can be integrated more easily into an existing cuff design without the need for new electrical connections or fastenings.

Figure 9:
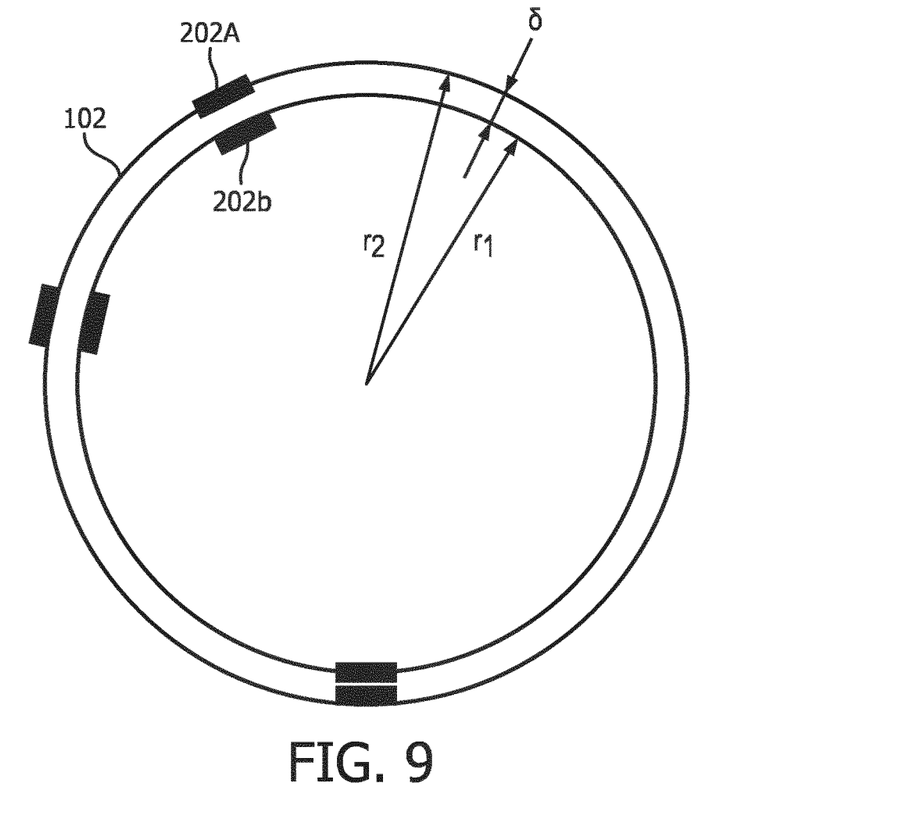
FIG. 9 shows another embodiment where pairs of coils are used to measure volume changes in a cuff.

In a further embodiment shown in FIG. 9, at least one pair of coils 202a, 202b are placed on opposing walls of cuff 102. Each coil has one or more windings. The first coil 202b is located on an inner surface of the cuff (the side closest to the body part in use) and the second coil 202a is located opposite to the first coil on an outer surface of the cuff (the side furthest from the body part in use) so that the coils are used to measure the distance between the inner surface and outer surface of the cuff 102. Changes in the volume of the body part of the subject change the distance between the first coil and the second coil, thus altering the mutual inductance of the coils or capacitance of the coils.

The parameter δ is the distance between the two cuff walls (inner surface and outer surface). δ is of the order of 0.5 cm for a cuff volume of 150 ml, although it will be appreciated that δ depends heavily on the design of the cuff. Using the default parameters $r_1$=5 cm (where $r_1$ is the radius of the body part/radius of the cuff to the inner surface) and dV=1 ml, it is estimated that the relative variation in δ is 0.6% and the relative variation in magnetic field from coil 202b at coil 202a is three times larger than this value i.e. 1.8%. Hence the change in B field is much larger than for the embodiment described with respect to FIG. 8 (~0.2%). The mutual inductance of the coils can be measured in a similar way to those in the embodiment of FIG. 8. Alternatively, the capacitance of a capacitor formed by the coils can be measured, with the capacitance being inversely proportional to the distance between the coils. A further advantage of this embodiment over that shown in is that the alignment of the coils with respect to each other is now more easily controlled.

As noted above, the apparatus 100 can be a volume-clamp based blood pressure monitor. As is known, volume clamp blood pressure monitors typically use a photoplethysmographic (PPG) sensor and an inflatable cuff on a finger. The cuff is continuously pressurized to follow the pressure of the artery in the finger using a closed-loop control system. The principle behind a volume-clamp BP monitoring device is that the pressure in the cuff is changed so as to keep the diameter of the artery (as measured by the PPG signal) constant. The required pressure changes needed to keep the diameter constant mirror the changes in arterial pressure and can therefore be used to calculate the blood pressure.

As described above however, PPG signals are influenced by a number of confounding parameters and the placement of the PPG sensor is critical since the light source has to be close to the artery (i.e. the palmar digital artery in the case that the cuff is wrapped around a finger).

Therefore, in some embodiments the apparatus 100 is a volume clamp blood pressure monitor comprising a plethysmography sensor 106 comprising a coil having one or more windings. The volume of the body part is measured using the plethysmography sensor 106 and the pressure in the cuff is changed to maintain a constant cross-sectional area of the coil. The inductance variations of the coil should therefore be measured with a frequency bandwidth of, for example 20-40 Hz.

The use of a plethysmography sensor 106 according to the invention in a volume-clamp based blood pressure monitor is advantageous as it removes the need for precise placement of the PPG sensor, and the volume measurements from the plethysmography sensor 106 are linearly proportional to volume, whereas PPG measurements are dependent on many parameters, the dependence being non-linear.

There is therefore provided an improved blood pressure monitor and method of determining the blood pressure of a subject that reduces or avoids some of the sources of error associated with conventional blood pressure monitors, particularly at low cuff pressures.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed

The invention claimed is:

1. A blood pressure monitor for use in measuring the blood pressure of a subject, the blood pressure monitor comprising:
 a cuff that is configured to be placed around a body part of the subject and inflated to apply pressure to the body part;
 a pressure sensor that is configured to provide measurements of the pressure in the cuff;
 a plethysmography sensor comprising two or more coils each having one or more windings, wherein the two or more coils are configured to be placed around the body part beneath the cuff such that changes in the volume of the body part beneath the cuff change the distance between the two or more coils, wherein an output signal of the plethysmography sensor comprises a measurement of a mutual inductance of the coils and
 a processing unit that is configured to determine the blood pressure of the subject from the measurements of the pressure in the cuff and the output signal indicating the volume of the body part beneath the cuff and/or the changes in the volume of the body part beneath the cuff.

2. A blood pressure monitor for use in measuring the blood pressure of a subject, the blood pressure monitor comprising:
 a cuff that is configured to be placed around a body part of the subject and inflated to apply pressure to the body part;
 a pressure sensor that is configured to provide measurements of the pressure in the cuff;
 a plethysmography sensor comprising a coil having one or more windings formed from wires of a conductive stretchable material or a piezoelectric material configured to be placed around the body part of the subject such that the body part beneath the cuff lies within the one or more windings, the plethysmography sensor providing an output signal comprising a measurement of the resistance of the coil, indicating the volume of the body part beneath the cuff and/or changes in the volume of the body part beneath the cuff change a cross-sectional area of the one or more windings; and
 a processing unit that is configured to determine the blood pressure of the subject from the measurements of the pressure in the cuff and the output signal indicating the volume of the body part beneath the cuff and/or the changes in the volume of the body part beneath the cuff.

3. A blood pressure monitor as claimed in claim 2, wherein the one or more windings of the coil can be stretched or compressed as the volume of the body part beneath the cuff changes.

4. A blood pressure monitor as claimed in claim 2, wherein the coil is part of a resonance circuit of an oscillator, and wherein the output signal of the plethysmography sensor comprises a measurement of a frequency of the oscillator.

5. A blood pressure monitor as claimed in claim 2, wherein the plethysmography sensor is integrated into the cuff.

6. A blood pressure monitor as claimed in claim 2, wherein the plethysmography sensor is configured to be placed around the body part beneath the cuff.

7. A blood pressure monitor as claimed in claim 6, wherein the plethysmography sensor is part of a stretchable band that is configured to be placed around the body part beneath the cuff.

8. A blood pressure monitor as claimed in claim 7, wherein the wires are arranged in the stretchable band to enable the one or more windings of the coil to be stretched or compressed as the volume of the body part beneath the cuff changes.

9. A method of measuring the blood pressure of a subject, the method comprising:
 placing a cuff around a body part of the subject and inflating the cuff to apply pressure to the body part;
 measuring the pressure in the cuff using a pressure sensor;
 measuring the volume of the body part beneath the cuff and/or changes in the volume of the body part beneath the cuff due to arterial pulsations using a plethysmography sensor comprising two or more coils each having one or more windings; wherein the step of measuring the volume of the body part beneath the cuff and/or changes in the volume of the body part beneath the cuff comprises measuring a mutual inductance of the coils and
 determining the blood pressure of the subject from measuring the pressure in the cuff and measuring the volume of the body part beneath the cuff and/or the changes in the volume of the body part beneath the cuff due to arterial pulsations.

10. A method as claimed in claim 9, wherein the method further comprises the step of:
 placing the plethysmography sensor around the body part beneath the cuff such that the body part lies within the one or more windings and changes in the volume of the body part of the subject change a cross-sectional area of the one or more windings.

* * * * *